(12) United States Patent
Mamedov

(10) Patent No.: US 10,532,962 B2
(45) Date of Patent: Jan. 14, 2020

(54) CONVERSION OF SHALE GAS TO AROMATICS

(71) Applicant: SABIC Global Technologies B.V., Bergen op Zoom (NL)

(72) Inventor: Aghaddin Kh. Mamedov, Houston, TX (US)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/072,254

(22) PCT Filed: Feb. 2, 2017

(86) PCT No.: PCT/US2017/016118
§ 371 (c)(1),
(2) Date: Jul. 24, 2018

(87) PCT Pub. No.: WO2017/136490
PCT Pub. Date: Aug. 10, 2017

(65) Prior Publication Data
US 2019/0031578 A1 Jan. 31, 2019

Related U.S. Application Data

(60) Provisional application No. 62/290,156, filed on Feb. 2, 2016.

(51) Int. Cl.
*C07C 2/76* (2006.01)
*C07C 51/363* (2006.01)

(52) U.S. Cl.
CPC .............. *C07C 2/76* (2013.01); *C07C 51/363* (2013.01); *C07C 2529/06* (2013.01);
(Continued)

(58) Field of Classification Search
CPC ..... C07C 2/76; C07C 51/363; C07C 2529/06; C07C 2529/076; C07C 2529/40; C07C 2529/48
See application file for complete search history.

(56) References Cited

U.S. PATENT DOCUMENTS 3,702,886 A   11/1972  Argauer et al.
5,936,135 A   8/1999   Choudhary et al.
(Continued)

FOREIGN PATENT DOCUMENTS

GB   1334243 A      10/1973
WO   2015035518 A1   3/2015
WO   2015117166 A1   8/2015

OTHER PUBLICATIONS

Anunziata, Oscar A., et al., "Catalytic conversion of natural gas with added ethane and LPG over Zn-ZSM-11", Applied Catalysis A: General, 2000, vol. 190, pp. 169-176.
(Continued)

*Primary Examiner* — Ali Z Fadhel
(74) *Attorney, Agent, or Firm* — Cantor Colburn LLP

(57) ABSTRACT

A method for converting shale gas to aromatic hydrocarbons includes passing a feedstock comprising ethane gas and methane gas to an aromatization reactor; converting a portion of the methane gas and ethane gas in the feedstock to liquid aromatic hydrocarbons with a zeolite based catalyst at a temperature of 750 C to 900 C; separating unconverted methane gas from liquid aromatic hydrocarbons; separating unconverted methane gas from the unconverted ethane gas; recycling the separated methane gas to the aromatization reactor; recovering aromatic hydrocarbons in a product stream after separation and removal from the aromatization reactor. Less than or equal to 95% of the ethane is converted to aromatic hydrocarbons.

19 Claims, 1 Drawing Sheet

(52) U.S. Cl.
CPC .... *C07C 2529/076* (2013.01); *C07C 2529/40* (2013.01); *C07C 2529/48* (2013.01)

(56) References Cited

U.S. PATENT DOCUMENTS

| | | |
|---|---|---|
| 6,943,131 B1 | 9/2005 | Ghosh et al. |
| 7,060,864 B2 | 6/2006 | Ghosh et al. |
| 7,279,608 B2 | 10/2007 | Ghosh et al. |
| 7,285,511 B2 | 10/2007 | Ghosh et al. |
| 7,304,194 B2 | 12/2007 | Ghosh et al. |
| 7,368,410 B2 | 5/2008 | Ghosh et al. |
| 7,399,727 B2 | 7/2008 | Ghosh et al. |
| 8,796,496 B2 | 8/2014 | Schneider et al. |
| 2008/0293980 A1* | 11/2008 | Kiesslich ............ B01J 29/46 585/408 |
| 2010/0331592 A1 | 12/2010 | Sangar et al. |
| 2014/0058144 A1 | 2/2014 | Bricker et al. |

OTHER PUBLICATIONS

Chen, L. et al.; "Dehydro-oligomerization of Methane to Ethylene and Aromatics over Molybdenum/HZSM-5 Catalyst" Journal of Catalysis 1995, vol. 157, pp. 190-200.

Chen, L. et al.; "Fourier Transform-Infrared Investigation of Adsorption of Methane and Carbon Monoxide on HZSM-5 and Mo/HZSM-5 Zeolites at Low Temperature", Journal of Catalysis, 1996, vol. 161, pp. 107-114.

Chen, L. et al.; "Promotional effect of Pt on non-oxidative methane transformation over Mo-HZSM-5 Catalyst", Catal. Lett. vol. 39, 1996, 169-172.

International Search Report for International Application No. PCT/US2017/016118; dated Apr. 17, 2017; 7 Pages.

Ma, Shuqi et al., "Recent Progress in methane dehydroaromatization: From laboratory curiosities to promissing technology", Journal of Energy Chemistry, 2013, vol. 22, pp. 1-20.

Shu, Y. et al.; "Promotional Effect of Ru on the Dehydrogenation and Aromatization of Methane in the Absence of Oxygen over Mo/HZSM-5 Catalysts" J. Catal, vol. 170, 1997, pp. 11-19.

Wang, D. et al.; "Characterization of a Mo/ZSM-5 Catalyst for the Conversion of Methane to Benzene"; Journal of Catalysis, 1997, vol. 169, pp. 347-358.

Wong, S. et al.; "Methane and Ethane Activation without adding oxygen: promotional effect of W in Mo-W/HZSM-5", Catalysis Letters, 1996, vol. 38, pp. 39-43.

Written Opinion of the International Search Report for International Application No. PCT/US2017/016118; dated Apr. 17, 2017; 5 Pages.

Xu, Y. et al.; "Dehydrogenation and aromatization of methane in the absence of oxygen on Mo/HZSM-5 catalysts before and after NH4OH extraction", Catalysis Letter, 1996, vol. 40, pp. 207-2014.

Xu, Y. et al.; "Methane activation without using oxidants over Mo/HZSM-5 zeolite catalysts" Catalysis Letter, 1995, vol. 30, pp. 135-149.

\* cited by examiner

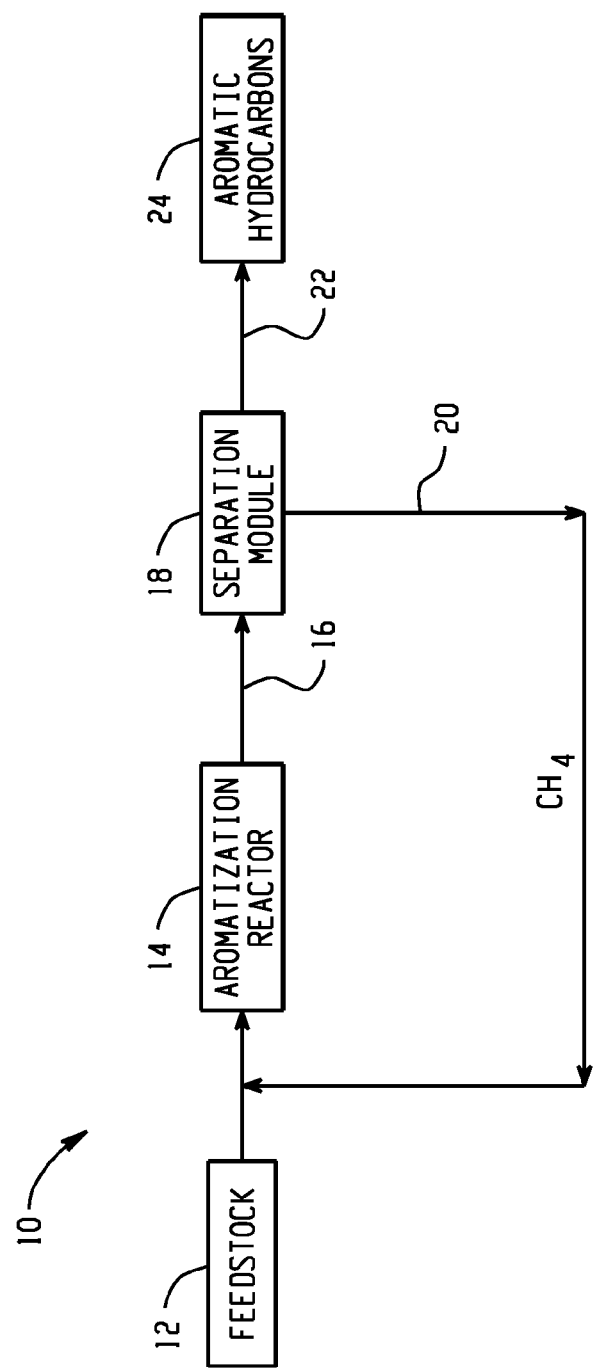

CONVERSION OF SHALE GAS TO AROMATICS

CROSS REFERENCE TO RELATED APPLICATIONS

This application is a 371 of International Application No. PCT/US2017/016118, filed Feb. 2, 2017, which claims priority to U.S. Application No. 62/290,156 filed Feb. 2, 2016, both of which are incorporated herein by reference in their entirety.

TECHNICAL FIELD

Disclosed herein is an improved process for the conversion of lower alkanes to aromatics. Specifically, the present disclosure is related to the simultaneous conversion of methane and ethane components of shale gas to aromatic hydrocarbons.

BACKGROUND

Aromatic hydrocarbons are an important commodity in the petroleum and petrochemical industries. The most commercially important aromatics include benzene, toluene, ethyl-benzene, and xylenes. Aromatics are conventionally produced by catalytic reforming of various petroleum feed stocks. For example, lower alkanes can be catalytically converted aromatics.

Shale gas contains approximately 15% of ethane. Conventionally, the methane and ethane are separately isolated from, for example, shale gas using a cryogenic method. Then the isolated methane is converted to aromatics and the isolated ethane is converted to aromatics in separate reaction systems, as they each require different reaction temperatures and possibly different catalysts. However, isolating the methane and ethane, as well as using different reaction systems is energy intensive.

Thus, there is a need for further improved processes for preparing aromatics from lower alkanes, which are more efficient and have a high yield of aromatic hydrocarbons.

BRIEF DESCRIPTION

The above described and other features are exemplified by the following FIGURES and detailed description.

A method for converting shale gas to aromatic hydrocarbons, comprises: passing a feedstock comprising ethane gas and methane gas to an aromatization reactor; converting a portion of the methane gas and ethane gas in the feedstock to liquid aromatic hydrocarbons with a zeolite based catalyst at a temperature of 750° C. to 900° C.; separating unconverted methane gas from liquid aromatic hydrocarbons; separating unconverted methane gas from the unconverted ethane gas; recycling the separated methane gas to the aromatization reactor; recovering aromatic hydrocarbons in a product stream after separation and removal from the aromatization reactor. Less than or equal to 95% of the ethane is converted to aromatic hydrocarbons.

A method for converting shale gas to aromatic hydrocarbons, comprises: passing a feedstock comprising 2% to 15% ethane gas and 85% to 98% methane gas to an aromatization reactor; converting a portion of the methane gas and ethane gas in the feedstock to liquid aromatic hydrocarbons with a zeolite based catalyst at a temperature of 750° C. to 900° C.; separating unconverted methane gas from liquid aromatic hydrocarbons and from the unconverted ethane gas; recycling the separated methane gas to the aromatization reactor; recovering aromatic hydrocarbons in a product stream after separation and removal from the aromatization reactor. The aromatic hydrocarbons yield per volume of the feedstock is increased by 20-25% as compared to a process without simultaneous conversion of ethane and methane to aromatic hydrocarbons.

BRIEF DESCRIPTION OF THE DRAWINGS

Refer now to the FIGURES, which are exemplary embodiments, and wherein the like elements are numbered alike.

FIG. 1 is a schematic of an embodiment of a method of producing aromatics.

DETAILED DESCRIPTION

The present disclosure provides a process allowing simultaneous conversion of methane and ethane from shale gas to aromatic hydrocarbons using a zeolite based catalyst. The simultaneous conversion of methane and ethane improves efficiency and allows an increase in aromatic production.

A method for converting shale gas to aromatics hydrocarbons can include passing a feedstock comprising gas, e.g., ethane gas and methane gas to an aromatization reactor. The feedstock can include 75 mole percent (mol %) to 98 mol % methane, for example, 75 mol % to 85 mol % methane, for example, 80 mol % to 90 mol % methane, for example, 85 mol % to 98 mol % methane. The feedstock can include 2 mol % to 25 mol % ethane, for example, 2 mol % to 15 mol % ethane, for example, 10 mol % to 25 mol % ethane, for example, 10 mol % to 20 mol % ethane. In an example, the feedstock can include 85 mol % to 98 mol % of methane gas and 2 mol % to 15 mol % of ethane gas. The feedstock can include hydrogen, steam, carbon monoxide, carbon dioxide, nitrogen, one or more noble gases, or a combination comprising at least one of the foregoing. For example, the feedstock can include 2% to 5% of carbon dioxide. In addition to methane and ethane, the feedstock can include propane, butane, pentane, carbon dioxide, oxygen, nitrogen, hydrogen sulfide, or a combination comprising at least one of the foregoing. In an example, the aromatization reaction can be nonoxidative, where the concentration of oxidizing agents such as oxygen or nitrogen oxides in the feedstream can be less than 5% by weight, less than 1% by weight, or less than 0.1% by weight. The feedstream can be free of oxygen. Free from oxygen as referred to herein means less than or equal to 500 parts per million oxygen atoms present.

The method can include converting a portion of the methane gas and ethane gas in the feedstock to liquid aromatic hydrocarbons in the aromatization reactor with a zeolite based catalyst at a temperature of 750° C. to 900° C. In an example, the temperature can be 750° C. to 850° C., for example, 775° C. to 825° C., for example, 800° C. to 825° C., for example, 800° C. to 850° C. The method can allow ethane conversion to occur at temperatures sufficient to allow methane conversion to aromatics. As a result, both the ethane and methane can be simultaneously converted to aromatics. The aromatic hydrocarbons can include benzene, toluene, ethylene-benzene, styrene, xylene, naphthalene, or a combination comprising at least one of the foregoing.

The aromatization reactor can include a zone, vessel, or chamber containing catalyst particles through which the feedstock flows and the reaction occurs. The reactor can involve a fixed, moving, or fluidized catalyst bed. In a fixed bed reactor, the catalyst remains stationary in the reactor and the catalyst particles are arranged in a vessel, for example, a vertical cylinder, with the reactants and products passing through the stationary bed. In a moving bed reactor, gravity causes the catalyst particles to flow while maintaining their relative positions to one another. The reactants can move through the bed with co-current, countercurrent, or cross-flow. In a fluidized bed reactor, gas is passed through the particular catalyst at high enough velocities to suspend the solid and cause it to behave as through it were a liquid. The catalyst can be supported by a porous plate. Feed rate of the gas can affect the hydrocarbon conversion. For example, with an increased feed rate, contact time is less, meaning less conversion.

The aromatization reaction can be performed at a pressure of 0 MegaPascals (MPa) to 10 MPa, for example, 0.1 MPa to 3 MPa, or 0.1 MPa to 0.5 MPa. The aromatization reaction can be performed at a gas hourly space velocity, volume of reactant flow/volume of the catalyst bed (GHSV) of 10 $h^{-1}$ to 10,000 $h^{-1}$. The space velocity of the aromatization reactor can be 1000 $h^{-1}$ to 4000 $h^{-1}$, for example, 2600 $h^{-1}$.

In an example, less than 20% of the methane in the feedstock can be converted to aromatic hydrocarbons. For example, less than 15%, for example, less than 10% of the methane can be converted to aromatic hydrocarbons. In an example, greater than 50% of the ethane in the feedstock can be converted to aromatic hydrocarbons. For example, greater than 60%, for example, greater than 65%, for example, greater than 70%, for example, greater than 80% of the ethane in the feedstock can be converted to aromatic hydrocarbons. In an example, 60% to 80%, for example, 65% of the ethane in the feedstock can be converted to aromatic hydrocarbons. In an example, 60% to 80% of the feedstock can be converted to aromatic hydrocarbons. For example, 65% of the feedstock, for example, 70% of the feedstock, for example, 75% of the feedstock, for example, 80% of the feedstock can be converted to aromatic hydrocarbons. The aromatic hydrocarbons yield per volume of the feedstock can be increased by 20-25% as compared to a process without simultaneous conversion of ethane and methane to aromatic hydrocarbons.

The unconverted methane gas can be separated from the liquid aromatic hydrocarbons and the unconverted methane gas can also be separated from the unconverted ethane gas in a separation unit. The term separation unit relates to the refinery unit that separates different compounds produced by the aromatization reactor. Compounds can be separated to separate streams in the separation unit. Any method for the separation of the unconverted reactants and products can be employed. Methods for separating methane from ethane and aromatics are well known and can involve distillation and/or extraction.

The separated unconverted methane gas can be recycled into the aromatization reactor. Due to the recycling of the unconverted methane gas into the aromatization reactor the yield of aromatic hydrocarbons is increased, as compared to a system without recycling.

The catalyst can include a metalosilicate as support, such as aluminum silicates, particularly zeolites. Zeolite is a crystalline hydrated aluminosilicate that can also contain other metals, such as sodium, calcium, barium, and potassium, and that has ion exchange properties. Examples of zeolites include ZSM-5, ZSM-11, ZSM-5/ZSM-11 intermediate, ZSM-12, ZSM-21, ZSM-22, ZSM-23, ZSM-35, ZSM-38, ZSM-48, ZSM-50, MCM-22, Zeolite L, Zeolite Beta and Mordenite.

ZSM-5 zeolite is a porous material containing an intersecting two-dimensional pore structure with 10-membered oxygen rings. Zeolites with such 10-membered oxygen ring pore structures can be classified as medium-pore zeolites. As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense.

ZSM-5 zeolite catalysts and their preparation are described in U.S. Pat. No. 3,702,886, which is herein incorporated by reference, in its entirety. As described herein and when used, the ZSM-5 zeolite catalyst can include those having a silica/alumina molar ratio of 200 or higher, for example, 250 to 500 prior to modification. The starting ZSM-5 can be an NH4+ or H+ form and may contain traces of other cations. Modification of ZSM-5-type zeolite with phosphorus-containing compounds can provide shape selective properties to the catalyst, yielding greater amounts of p-xylene than the thermodynamic equilibrium value when used in ethane and methane conversion to aromatics compared to unmodified catalysts.

The ZSM-5-type zeolite can be modified by treating with phosphorus-containing compounds including, but not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4)_2HPO_4$) can be used as the phosphorus-containing compound to provide a catalyst for with shape selective properties to provide increased p-xylene selectivity. Such modified catalysts can contain phosphorus (P) in an amount of 0.01 to 0.15 g P/g zeolite, for example, 0.02 to 0.13 g P/g zeolite, and for example, 0.07 g P/g zeolite to 0.12 g P/g zeolite, and for example, 0.09 g P/g zeolite to 0.11 g P/g zeolite. After phosphorus treatment, the phosphorus-treated zeolite can be dried.

The P-modified ZSM-5 catalyst can be contacted with an appropriate feed of an aromatic hydrocarbon and an alkylating agent under alkylation reaction conditions to carry out aromatic alkylation. A gas co-feed can be used. The co-feed gas can include hydrogen or an inert gas In addition to any co-feed gas, water in the form of steam can be introduced into the reactor as co-feed along with the alkylation feed. The water or steam used for the methylation and/or ethylation reaction can be introduced with or without hydrogen or inert gas as co-feed with the alkylation feed to the reactor during the startup of the alkylation reaction, or it can be introduced subsequent to initial startup. In either case, liquid water can be added and vaporized prior to its mixing with co-feed gas (if any) and the alkylation feed. The use of water co-feed is described in U.S. Pat. No. 7,060,864 and in U.S. Pat. No. 7,279,608, both of which are herein incorporated by reference, in its entirety.

The reactor pressure for alkylation can vary, but generally has a value of 65 kiloPascals (kPa) to 7000 kPa (10 psig to 1000 psig). Reactor temperatures can vary, but generally have a value of 400° C. to 700° C. Upon introduction of feed into the reactor, the catalyst bed temperature can be adjusted to a selected reaction temperature to effect a desired conversion. The temperature can be increased gradually at a rate of 1° C./minute to 10° C./minute to provide the desired final reactor temperature.

The phosphorus-modified ZSM-5 can be made by forming a slurry of a ZSM-5-type zeolite and an aqueous solution of a phosphorus compound and removing water from the slurry to form a phosphorus-modified ZSM-5 zeolite. The phosphorus-modified catalyst prepared as described in U.S. Pat. No. 7,285,511, which is hereby incorporated by reference, in its entirety, is not steamed and has a pore volume of from 0.2 ml/g or less.

The phosphorus-modified ZSM-5 can be made by dissolving alumina in a phosphorus-containing acid solution and treating the zeolite with the dissolved alumina solution as described in U.S. Pat. No. 6,943,131, which is hereby incorporated by reference, in its entirety.

The phosphorus-modified ZSM-5 can have particular 31P MAS NMR peaks indicating the present of free phosphate, phosphate bonded to extra-framework aluminum, or particular phosphate species as described in Published U.S. Pat. No. 7,399,727, which is hereby incorporated by reference, in its entirety. The catalyst can exhibit at least two 31P MAS NMR peaks having maxima at 0 ppm to −55 ppm. For example, the catalyst can exhibit a 31P MAS NMR peak having a maximum at 0 ppm to −25 ppm, for example, at −5 ppm to −20 ppm, and another with a maximum at −40 ppm to −50 ppm. Such peaks are an indication of various phosphorus species.

Zeolites other than ZSM-5 which can be used in the process disclosed herein can include medium pore zeolites that have 10 and/or 12 member ring channels system, such as ZSM-4 (Zeolite Omega), ZSM-11, ZSM-12, ZSM-22, ZSM-23, Zeolite Beta, Mordenite, MCM-22, or a combination comprising at least one of the foregoing. Silica-alumina phosphates (SAPO), aluminum phosphates (AlPO) or a combination comprising at least one of the foregoing can be desired in the process disclosed herein.

The phosphorus-modified zeolite can be heated at 300° C. or higher after phosphorus treatment and then combined with an inorganic oxide binder material to form a zeolite-binder mixture which forms a bound zeolite catalyst as described in U.S. Pat. No. 7,368,410, which is hereby incorporated by reference, in its entirety.

The phosphorus-modified zeolite catalyst can be combined with an inorganic oxide binder material which has been treated with a mineral acid to form a zeolite-binder mixture and heating the zeolite-binder mixture at temperature of 400° C. or higher to form a bound zeolite catalyst as described in U.S. Pat. No. 7,368,410, which is hereby incorporated by reference, in its entirety.

The bound P-modified zeolite catalyst can be mildly steamed at a temperature of 300° C. or lower before using the catalyst in any reaction. The steaming can be carried out in-situ or ex-situ of the reactor. The use of catalyst steaming at mild temperatures is described in U.S. Pat. No. 7,304,194, which is herein incorporated by reference, in its entirety.

The P-modified ZSM-5 catalyst can be contacted with an appropriate feed of alkylation process reactants, such as an aromatic hydrocarbon and an alkylating agent, under process conditions to produce an alkylated aromatic product.

The zeolite catalyst precursor as used herein can have a medium-pore size including a pore size of 5-6 Å. Medium pore size zeolites can include 10-ring zeolites. The zeolite can be a pentasil type. The zeolite catalyst precursor can be ZSM-5, ZSM-22, ZSM-8, ZSM-11, ZSM-12, ZSM-23, ZSM-35, or a combination comprising at least one of the foregoing. The catalyst can contain promoters. Examples of promoters include W, Zn, Ga, Cr, or a combination comprising at least one of the foregoing.

The zeolite catalyst precursors can be prepared in any desired method. For example, zeolites can be formed from alkali metal aluminate, alkali metal silicate, and amorphous $SiO_2$ under hydrothermal conditions. In an example, the zeolite catalyst precursor can be prepared on silicon dioxide using a fusing method. The zeolite catalyst precursor can be produced by depositing Mo and optionally one or more additional elements selected from the Group 6-11 of the Periodic Table on the zeolite using an incipient wetness method which includes the contacting zeolite with a solution comprising one or more additional elements selected from the Group 6-11 of the Periodic Table, and drying the zeolite to provide a zeolite catalyst precursor. Deposition of metal(s) onto the zeolite can also be carried out by using impregnation techniques in aqueous solution under acidic as well as basic conditions.

The metal(s) can be deposited on the zeolite catalyst precursor concurrently by contacting the zeolite with a solution comprising, for example, a soluble Mo-salt and one or more soluble salts comprising one or more additional elements from the Group 6-11 of the Periodic Table. Alternatively, the Mo and one or more additional elements can be deposited on the zeolite catalyst precursor subsequently by contacting the zeolite catalyst precursor with a solution comprising Mo and a different solution comprising one or more additional elements selected from Group 6-11 of the Periodic Table. When one or more additional elements are deposited, it is preferred that Mo is deposited first. The solution used for depositing the Mo and optional additional elements can be an aqueous solution. The zeolite catalyst precursor can be dried and calcined to form the catalyst. The zeolite catalyst precursor can be calcined at 500° C. to 650° C. and a pressure of 0.101 MPa for 1-5 hours. In an example, the zeolite catalyst precursor is calcined at 600° C. for 2 hours.

Exemplary catalysts that can be used included, but are not limited to W-Zn/ZSM-5, Mo/ZSM-5, or a combination comprising at least one of the foregoing.

As illustrated in FIG. 1, an embodiment of the method 10 can include providing a feedstock 12 to an aromatization reactor 14. A first product stream 16 can exit the aromatization reactor 14. The first product stream 16 can include aromatic hydrocarbons, unconverted methane gas, unconverted ethane gas, or a combination comprising at least one of the foregoing. The first product stream 16 can be directed to a separation module 18 that can separate unconverted methane gas from both the aromatic hydrocarbons and the unconverted ethane gas. The separation module 18 can produce a second product stream 20 containing unconverted methane gas and a third product stream 22 containing any unreacted ethane gas and the aromatic hydrocarbons 24. The aromatic hydrocarbons 24 can be purified to remove any unreacted ethane gas.

The methods disclosed herein include at least the following embodiments:

Embodiment 1

A method for converting shale gas to aromatic hydrocarbons, comprising: passing a feedstock comprising ethane gas and methane gas to an aromatization reactor; converting a portion of the methane gas and ethane gas in the feedstock to liquid aromatic hydrocarbons with a zeolite based catalyst at a temperature of 750° C. to 900° C.; separating unconverted methane gas from liquid aromatic hydrocarbons; separating unconverted methane gas from the unconverted ethane gas; recycling the separated methane gas to the aromatization reactor; recovering aromatic hydrocarbons in a product stream after separation and removal from the aromatization reactor; wherein less than or equal to 95% of the ethane is converted to aromatic hydrocarbons.

Embodiment 2

The method of Embodiment 1, wherein the feedstock is a shale gas feedstock.

Embodiment 3

The method of Embodiment 1 or Embodiment 2, wherein the feedstock further comprises propane, butane, pentane, carbon dioxide, oxygen, nitrogen, hydrogen sulfide, or a combination comprising at least one of the foregoing.

Embodiment 4

The method of any of Embodiments 1-3, wherein the feedstock comprises 75-85 mol % methane.

Embodiment 5

The method of any of Embodiments 1-4, wherein the feedstock comprises 10-25 mol % ethane.

Embodiment 6

The method of any of Embodiments 1-5, wherein less than or equal to 10% of the methane is converted to aromatic hydrocarbons.

Embodiment 7

The method of any of Embodiments 1-6, wherein the space velocity of the aromatization reactor is 1000 $h^{-1}$ to 4000 $h^{-1}$.

Embodiment 8

The method of any of Embodiments 1-7, wherein the space velocity of the aromatization reactor is 2600 $h^{-1}$.

Embodiment 9

The method of Embodiment 1 or Embodiment 2, wherein the zeolite catalyst is contacted with a molybdenum compound and calcined to form a catalyst.

Embodiment 10

The method of any of Embodiments 1-9, wherein the zeolite comprises ZSM-5, ZSM-22, ZSM-8, ZSM-11, ZSM-12, ZSM-23, ZSM-35, or a combination comprising at least one of the foregoing.

Embodiment 11

The method of Embodiment 10, wherein the zeolite is a ZSM-5 zeolite.

Embodiment 12

The method of any of Embodiments 1-11, wherein the catalyst is prepared on silicon dioxide using a fusing method.

Embodiment 13

The method of any of Embodiments 10-12, wherein the catalyst is prepared by mixing silicon dioxide and the ZSM-5 zeolite.

Embodiment 14

The method of any of Embodiments 1-13, wherein the catalyst contains promoters comprising W, Zn, Ga, Cr, or a combination comprising at least one of the foregoing.

Embodiment 15

The process of any of Embodiments 1-14, wherein conversion occurs at a temperature of 800° C. to 850° C.

Embodiment 16

The method of any of Embodiments 1-15, wherein the aromatic hydrocarbons comprise toluene, benzene, naphthalene, xylene or a combination comprising at least one of the foregoing.

Embodiment 17

The method of any of Embodiments 1-16, wherein the aromatic hydrocarbons yield per volume of the feedstock is increased by 20-25% as compared to a process without simultaneous conversion of ethane and methane to aromatic hydrocarbons.

Embodiment 18

The method of any of Embodiments 1-17, wherein 70% of the feedstock is converted to aromatic hydrocarbons.

Embodiment 19

A method for converting shale gas to aromatic hydrocarbons, comprising: passing a feedstock comprising 2% to 15% ethane gas and 85% to 98% methane gas to an aromatization reactor; converting a portion of the methane gas and ethane gas in the feedstock to liquid aromatic hydrocarbons with a zeolite based catalyst at a temperature of 750° C. to 900° C.; separating unconverted methane gas from liquid aromatic hydrocarbons and from the unconverted ethane gas; recycling the separated methane gas to the aromatization reactor; recovering aromatic hydrocarbons in a product stream after separation and removal from the aromatization reactor; wherein the aromatic hydrocarbons yield per volume of the feedstock is increased by 20-25% as compared to a process without simultaneous conversion of ethane and methane to aromatic hydrocarbons.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %,"

etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for converting methane and ethane to aromatic hydrocarbons, comprising:
    passing a feedstock comprising ethane gas and methane gas to an aromatization reactor;
    aromatizing less than 20 wt % of the methane gas and greater than 50 wt % of the ethane gas in the feedstock with a catalyst comprising a zeolite at a temperature of 750° C. to 900° C. to produce a product stream comprising aromatic hydrocarbons, unconverted methane, and unconverted ethane;
    separating an unconverted methane gas stream from the product stream;
    recycling the separated unconverted methane gas stream to the aromatization reactor; and
    recovering the aromatic hydrocarbons in the product stream.

2. The method of claim 1, wherein the feedstock is a shale gas feedstock.

3. The method of claim 1, wherein the feedstock further comprises propane, butane, pentane, carbon dioxide, oxygen, nitrogen, hydrogen sulfide, or a combination comprising at least one of the foregoing.

4. The method of claim 1, wherein the feedstock comprises 75-85 mol % methane.

5. The method of claim 1, wherein the feedstock comprises 10-25 mol % ethane.

6. The method of claim 1, wherein the gas hourly space velocity of the aromatization reactor is 1000 $h^{-1}$ to 4000 $h^{-1}$.

7. The method of claim 1, wherein the gas hourly space velocity of the aromatization reactor is 2600 $h^{-1}$.

8. The method of claim 1, wherein the zeolite is prepared by contacting a zeolite precursor with a molybdenum compound followed by calcining.

9. The method of claim 1, wherein the zeolite comprises ZSM-5, ZSM-22, ZSM-8, ZSM-11, ZSM-12, ZSM-23, ZSM-35, or a combination comprising at least one of the foregoing.

10. The method of claim 9, wherein the zeolite is a ZSM-5 zeolite.

11. The method of claim 10, wherein the catalyst is prepared by mixing silicon dioxide and the ZSM-5 zeolite.

12. The method of claim 1, wherein the catalyst further comprises fused silicon dioxide.

13. The method of claim 1, wherein the catalyst contains promoters comprising W, Zn, Ga, Cr, or a combination comprising at least one of the foregoing.

14. The process of claim 1, wherein the aromatizing occurs at the temperature of 800° C. to 850° C.

15. The method of claim 1, wherein the aromatic hydrocarbons comprise toluene, benzene, naphthalene, xylene or a combination comprising at least one of the foregoing.

16. The method of claim 1, wherein the aromatic hydrocarbons yield per volume of the feedstock is increased by 20-25% as compared to a process without simultaneous conversion of ethane and methane to aromatic hydrocarbons.

17. The method of claim 1, wherein 70% of the feedstock is converted to aromatic hydrocarbons.

18. A method for converting methane and ethane to aromatic hydrocarbons, comprising:
    passing a feedstock comprising 2 mole % to 15 mole % ethane gas and 85 mole % to 98 mole % methane gas to an aromatization reactor;
    aromatizing less than 20 wt % of the methane gas and greater than 50 wt % of the ethane gas in the feedstock with a catalyst comprising a zeolite at a temperature of 750° C. to 900° C. to produce a product stream comprising aromatic hydrocarbons, unconverted methane, and unconverted ethane;
    separating an unconverted methane gas stream from the product stream;
    recycling the separated unconverted methane gas stream to the aromatization reactor; and
    recovering the aromatic hydrocarbons in the product stream;
    wherein the aromatic hydrocarbons yield per volume of the feedstock is increased by 20-25% as compared to a process without simultaneous conversion of ethane and methane to aromatic hydrocarbons.

19. The method of claim 18, wherein the separating comprises distilling and/or extracting for the separation of the unconverted methane gas stream from the product stream.

* * * * *